United States Patent
Saiki

(10) Patent No.: US 7,919,642 B2
(45) Date of Patent: Apr. 5, 2011

(54) SILAHYDROCARBYL ESTERS OF 3-CHLORO-2-TRIFLUOROMETHYLPROPIONIC ACID, THEIR PREPARATION AND PREPARATION OF THE CORRESPONDING ACRYLIC ACID ESTERS

(75) Inventor: Takeaki Saiki, Hiratsuka (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 0 days.

(21) Appl. No.: 12/810,390

(22) PCT Filed: Dec. 22, 2008

(86) PCT No.: PCT/JP2008/073912
§ 371 (c)(1),
(2), (4) Date: Aug. 19, 2010

(87) PCT Pub. No.: WO2009/082027
PCT Pub. Date: Jul. 2, 2009

(65) Prior Publication Data
US 2010/0311999 A1  Dec. 9, 2010

(30) Foreign Application Priority Data
Dec. 26, 2007 (JP) .................................. 2007-334930

(51) Int. Cl.
*C07F 7/04* (2006.01)
(52) U.S. Cl. ..................................................... 556/440
(58) Field of Classification Search ................... 556/440
See application file for complete search history.

(56) References Cited

U.S. PATENT DOCUMENTS
4,965,387 A  10/1990  Shinohara et al.

FOREIGN PATENT DOCUMENTS
| EP | 1637514 A1 | 3/2006 |
| JP | 2250888 A | 10/1990 |
| JP | 2000-248114 A | 9/2000 |
| JP | 2002-322214 A | 11/2002 |

OTHER PUBLICATIONS

English language abstract for JP 2250888 extracted from espacenet.com database, dated Oct. 25, 2010, 4 pages.
English language translation and abstract for JP 2000-248114 extracted from PAJ database, dated Oct. 25, 2010, 32 pages.
English language translation and abstract for JP 2002-322214 extracted from PAJ database, dated Oct. 25, 2010, 64 pages.
PCT International Search Report for PCT/JP2008/073912, dated May 12, 2009, 3 pages.

*Primary Examiner* — Jafar Parsa
(74) *Attorney, Agent, or Firm* — Howard & Howard Attorneys PLLC

(57) ABSTRACT

An organic silicon compound represented by the following general formula: $ClCH_2CH(CF_3)COOR^3Si(R^1)_n(R^2)_{3-n}$ (wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^3$ designates substituted or unsubstituted alkylene groups having 1 to 20 carbon atoms, and "n" is an integer from 0 to 3). The organic silicon compound is suitable for use as a preferable precursor in the manufacture of silanes that contain (2-trifluoromethylacryloxy)alkyl groups.

4 Claims, 1 Drawing Sheet

SILAHYDROCARBYL ESTERS OF 3-CHLORO-2-TRIFLUOROMETHYLPROPIONIC ACID, THEIR PREPARATION AND PREPARATION OF THE CORRESPONDING ACRYLIC ACID ESTERS

RELATED APPLICATIONS

This application claims priority to and all the advantages of International Patent Application No. PCT/JP2008/073912, filed on Dec. 22, 2008, which claims priority to Japanese Patent Application No. 2007-334930, filed on Dec. 26, 2007.

TECHNICAL FIELD

The present invention relates to an organic silicon compound and to a method of manufacturing thereof, in particular, to a silicon compound that contains a (2-trifluoromethyl-3-chloropropionoxy)alkyl group. The invention also relates to a method of manufacturing the last-mentioned compound, as well as to a method of manufacturing a silicon compound that contains (2-trifluoromethylakryloxy)alkyl group.

BACKGROUND ART

It is expected that acrylic acid silylalkyl esters that contain cyano groups, trifluoromethyl groups, or similar electron-attracting groups in the 2-position may find use as starting materials for adhesives or polymer monomers (see Japanese Unexamined Patent Application Publication (Kokai) H2-250888 and Japanese Unexamined Patent Application Publication (Kokai) 2002-322214). However, such compounds or intermediate products thereof encounter problems in manufacturing and handling because of their anion-polymerization properties and can easily polymerize due to moisture.

For example, there is a risk that the reaction that takes place in the manufacture of a silicon compound having (2-trifluoromethylacryloxy)alkyl groups between 2-trifluoromethyl acrylic acid chloride and silanes which contain silicon-bonded hydroxyalkyl groups may be accompanied either by polymerization of the acrylic compound in the positions of polymerizable double bonds, or by occurrence of a condensation reaction between hydroxyl groups and silicon-bonded hydrolysable bonds, if the target silicon compound contains silicon-bonded hydrolysable groups.

DISCLOSURE OF INVENTION

It is an object of the present invention to provide a silicon compound which contains a (2-trifluoromethyl-3-chloropropionoxy)alkyl group and is suitable for use as a preferable precursor in the manufacture of silanes that contain (2-trifluoromethylacryloxy) alkyl groups. It is another object to provide a method of manufacturing a silicon compound that contains a (2-trifluoromethylakryloxy)alkyl group, the method being characterized by using a silicon compound that contains a (2-trifluoromethyl-3-chlkoropropionoxy)alkyl group and retards occurrence of polymerization in the manufacturing process.

More specifically, the invention provides an organic silicon compound represented by the following general formula:

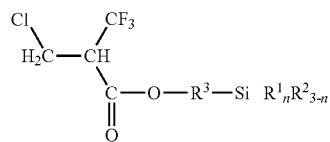

(wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^3$ designates substituted or unsubstituted alkylene groups having 1 to 20 carbon atoms, and "n" is an integer from 0 to 3). The invention also provides a method of manufacturing an organic silicon compound represented by the following general formula:

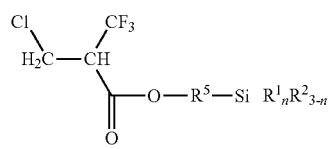

(wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^5$ designates substituted or unsubstituted alkylene groups having 2 to 20 carbon atoms, and "n" is an integer from 0 to 3), the method being characterized by carrying out a reaction between a compound of the following general formula:

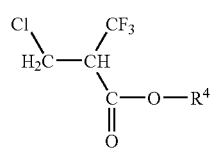

(wherein, $R^4$ designates an alkenyl group with 2 to 20 carbon atoms) and a silicon compound having silicon-bonded hydrogen atoms and represented by the following general formula:

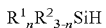

(wherein, $R^1$ and $R^2$, and "n" are the same as defined above), the reaction being carried out in the presence of a hydrosilylation catalyst. The invention further provides a method of manufacturing an organic silicon compound that contains a (2-trifluoromethylacryloxy)alkyl group and is represented by the following general formula:

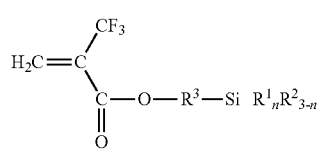

(wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^3$ designates substituted or unsubstituted alkyene groups having 1 to 20 carbon atoms, and "n" is an integer from 0 to 3), the method being characterized by carrying out a reaction between a basic compound and an organic silicon compound of the following general formula:

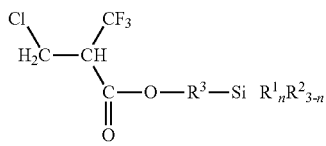

(wherein, $R^1$, $R^2$, $R^3$, and "n" are the same as defined above).

The organic silicon compound of the invention is easy to handle since the positions of the polymerizable double bonds of the appropriately structured acrylic compound are protected with hydrogen chloride. Furthermore, the hydrogen chloride added to the aforementioned polymerizable double-bond position can be easily disconnected by using a base so that the polymerizable double bond can be recovered. In view of the above, the compound of the invention is suitable for use as a precursor of a silicon compound that contains (2-trifluoromethylacryloxy)alkyl group.

The method of the invention for manufacturing the organic silicon compound of the invention makes it possible to easily and efficiently produce a silicon compound that contains a (2-trifluoromethyl-3-chloropropionoxy)alkyl group. In particular, there is no risk of occurrence of a condensation reaction when the aforementioned organic silicon compound contains silicon-bonded hydrolysable groups or silicon-bonded halogen atoms.

The method of the invention for manufacturing a silicon compound that contains a (2-trifluoromethylacryloxy)alkyl group allows manufacturing of the aforementioned compound in a simple and efficient manner.

BEST MODE FOR CARRYING OUT THE INVENTION

The present invention will be further described in more detail.

The organic silicon compound of the invention is represented by the following general formula:

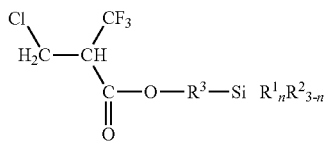

In this formula, $R^1$ represents independently from each other the same or different univalent hydrocarbon groups having 1 to 20 carbon atoms. Such groups can be exemplified by the following: methyl, ethyl, n-propyl, isopropyl, isobutyl, sec-butyl, t-butyl, or a similar alkyl group; cyclopentyl, cyclohexyl, 2-methylcyclohexyl, norbornyl, or a similar cyclic alkyl group; phenyl, tolyl, or a similar aryl group; vinyl, allyl, hexenyl, or a similar alkenyl group; chloromethyl, chloropropyl, 3,3,3-trifluoropropyl, or a similar halogenated alkyl group. Of these, unsubstituted alkyl groups or aryl groups with 1 to 20 carbon atoms are preferable, especially methyl and phenyl groups are most preferable. $R^2$ represents independently from each other the same or different hydrolysable groups having 1 to 20 carbon atoms, or halogen atoms. The hydrolysable groups with 1 to 20 carbon atoms are exemplified by groups selected from alkoxy groups or alkyloxyalkoxy groups. The alkoxy groups having 1 to 20 carbon atoms can be exemplified by methoxy, ethoxy, propoxy, isopropoxy, butoxy, isobutoxy, sec-butoxy, t-butoxy, hexyloxy, 2-ethylhexyloxy, octyloxy, decyloxy, undecyloxy, or octadecyloxy groups, of which the methoxy and ethoxy groups are preferable. The alkyloxyalkoxy groups with 2 to 20 carbon atoms are represented by methyloxymethoxy, methyloxyethoxy, ethyloxymethoxy, ethyloxyethoxy, methyloxypropoxy, ethyloxypropoxy, or propyloxypropoxy groups, of which the methyloxymethoxy and methyloxyethoxy groups are preferable. Halogen atoms are exemplified by fluorine, chlorine, or bromine atoms, of which the chlorine atom is preferable. $R^3$ represents an alkylene group having 1 to 20 carbon atoms, preferably an alkylene group with 2 to 10 carbon atoms, and most preferably an alkylene group with 3 to 5 carbon atoms. Specific examples are the following: methylene, ethylene, n-propylene, isopropylene, or isobutylene groups, of which the n-propylene groups or isopropylene groups are preferable; "n" is an integer from 0 to 3, preferably from 0 to 2, and most preferably 0 or 1.

The organic silicon compound of the invention can be produced by causing a reaction between a chloride 2-trifluoromethyl-3-chloropropionate and a silane that contains a silicon-bonded hydroxyalkyl group, but a preferable method for obtaining the aforementioned compound is a reaction conducted in the presence of a hydrosilylation catalyst between a compound of the following general formula:

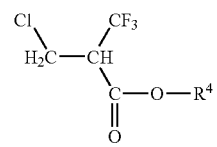

and a silicon compound that has a silicon-bonded hydrogen atom and is represented by the following general formula:

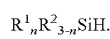

$R^1{}_nR^2{}_{3-n}SiH.$

When the final product contains a silicon-bonded hydrolysable group or a silicon-bonded halogen atom, the last-mentioned method makes it possible to efficiently obtain an organic silicon compound of high purity without a risk of occurrence of a condensation reaction. In the above formula, $R^1$, $R^2$, and "n" have the same meanings as mentioned above; and $R^4$ designates an alkenyl group with 2 to 20 carbon atoms and can be exemplified by vinyl, allyl, isopropenyl, or hexenyl group, of which allyl groups are preferable.

For efficiency of the reaction, it is recommended that in the reaction the silicon compound having silicon-bonded hydrogen atoms be used in the amount of 0.5 to 2.0 moles, preferably 0.9 to 1.2 moles per 1 mole of the compound of the following general formula:

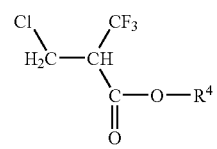

In order to conduct the reaction more efficiency and to reach a preferable speed of the reaction, it is recommended to conduct the reaction at a temperature in the range of 20 to 200° C. There are no special needs for use of solvent, but in order to keep the reaction product in a uniform state and for providing a predetermined viscosity, a solvent can be used in the reaction. The solvent should not be harmful to the reaction, and as much as possible should be excluded from participation in the reaction itself. For example, the solvent may be a saturated aliphatic hydrocarbon type solvent, an aromatic hydrocarbon type solvent, or an alkyl-ether type solvent. In order to efficiently suppress generation of byproducts, it is recommended to conduct the reaction in the atmosphere of inert gas, such as nitrogen. Normally, the obtained organic silicon compound of the invention is easily separated from the reaction system and purified by distillation.

The compound of the following general formula:

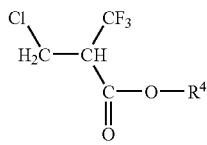

can be easily prepared, e.g., by causing a reaction between a 2-trifluoromethyl acrylic acid chloride and a 2-methyl-1-propenol, or allyl alcohol with 2 to 20 carbon atoms, or a similar alkenyl-containing alcohol. If the reaction is carried out between the 2-trifluoromethyl acrylic acid chloride and the alkenyl-containing alcohol, a preferable reaction speed can be efficiently reached by heating the reaction system to an appropriate temperature in the range of 20 to 100° C. For efficiency of the reaction, it is preferable that the alkenyl-containing alcohol be used in the amount of 0.5 to 2.0 moles, preferably 0.9 to 1.2 moles per 1 mole of the 2-trifluoromethylacrylic acid chloride. A commercially produced 2-trifluoromethyl acrylic acid chloride can be used for the purposes of the invention, and the reaction can be carried out also between a 2-trifluoromethylacrylic acid and thionyl chloride for preparing 2-trifluoromethyl acrylic acid chloride.

The silicon compound having silicon-bonded hydrogen atoms and expressed by the following formula:

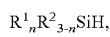

can be exemplified by the following: trimethoxysilane, triethoxysilane, triisopropoxysilane, trimethylsilane, methyldimethoxysilane, methyldiethoxysilane, dimethylmethoxysilane, dimethylethoxysilane, phenyldimethoxysilane, or chloromethyldimethoxysilane.

The hydrosilylation catalyst may be a conventional one known in the art and can be represented, e.g., by chloroplatinic acid, an alcohol solution of chloroplatinic acid, a complex of a chloroplatinic acid with an olefin, vinylsiloxane, or an acetylene compound, platinum black, platinum on the surface of a hard carrier, or a similar platinum-system compound; tetrakis(triphenylphosphine)palladium, or a similar palladium-system compound; chlorotris(triphenylphosphine)rhodium, or a similar rhodium-system compound; or an iridium-system catalyst, e.g., of the type represented by the following formulae: Ir(OOCCH$_3$)$_3$, Ir(C$_5$H$_7$O$_2$), etc. The platinum-system catalysts are preferable. Catalysts of two or more types can be used in combination.

There are no special limitations with regard to amounts in which the hydrosilylation catalyst can be used, provided that the hydrosilylation reaction is accelerated. It can be recommended, however, to use this catalyst in concentration of 0.000001 to 1 mole %, and preferably 0.0004 to 0.01 mole %. If the catalyst is used in an amount below the recommended lower limit, the effect of the catalyst may be very low and may not accelerate the reaction. If, on the other hand, the added amount exceeds the recommended upper limit, this will be economically unjustifiable.

The organic silicon compound of the invention can be mixed with a basic compound for dehydrochlorination and turning it into a silicon compound that contains a (2-trifluoromethylacryloxy)alkyl group and is represented by the following general formula:

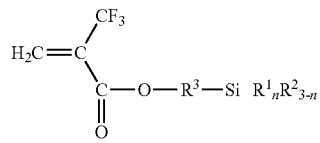

(wherein R$^1$, R$^2$, R$^3$, and "n" are the same as defined above). For efficient dehydrochlorination, the process can be carried out at an appropriate temperature in the range of −20° C. to 100° C. A solvent in not specifically needed for dehydrochlorination but can be used in this process for maintaining the reaction product in a uniform state and for providing an appropriate viscosity. The solvent should not be harmful to the reaction, and as much as possible should be excluded from participation in the reaction itself. For example, the solvent may be a saturated aliphatic hydrocarbon type solvent, an aromatic hydrocarbon type solvent, or an alkyl-ether type solvent. In order to efficiently suppress generation of byproducts, it is recommended to conduct the reaction in an atmosphere of inert gas, such as nitrogen.

The basic compound can be exemplified by triethylamine, pyridine, 2-picoline, 1,4-diazabicyclo[2,2,2]octane, 4-dimethylaminopyridine, or a similar tertiary amine compound; sodium hydroxide, potassium hydroxide, or a similar inorganic base. It is preferable to use a tertiary amine compound, especially triethylamine. This is because such a basic compound is liquid at room temperature and is easy to handle.

EXAMPLES

The invention will be further described with reference to specific practical and comparative examples, wherein the practical examples should not be construed as limiting the scope of the invention.

Practical Example 1

12.1 g (0.21 mole) of allyl alcohol were added dropwise at room temperature and in a flow of nitrogen to 30.6 g (0.19 mole) of 2-trifluoromethyl acrylic acid chloride, and after addition of the allyl alcohol was completed, the components were stirred for 8 hours at 50° C. Gas chromatography confirmed formation of allyl 1-chloro-2-trifluoromethylpropionate, and a non-reacted substance was removed by distillation under a reduced pressure. The product was combined with 0.04 g of a 10% isopropanol solution of a chloroplatinic acid, and 32.8 g (0.2 moles) of triethoxysilane were added dropwise at 70° C. Following this, the product was stirred for 2 hours at 100° C., and the reaction mixture was subjected to distillation to produce 25.7 g of 3-(2'-trifluoromethyl-3'-chloropropionoxy)propyltriethoxysilane. The $^1$H-NMR spectrum of the obtained product is shown in FIG. 1. The yield was 36%, and the boiling point of the obtained compound was 118° C./2 mm Hg.

Practical Example 2

1 g (2.6 mmol) of the 3-(2'-trifluoromethyl-3'-chloropropionoxy)propyltriethoxysilane obtained in Practical Example 1 was dissolved in 5 g of toluene. The solution was combined with 0.27 g (2.6 mmol) of triethylamine, and the salt precipitated. Gas chromatography confirmed that the product comprised 3-(2'-trifluoromethylacryloxy)propyltriethoxysilane obtained with a yield of 95%.

Figure 1:
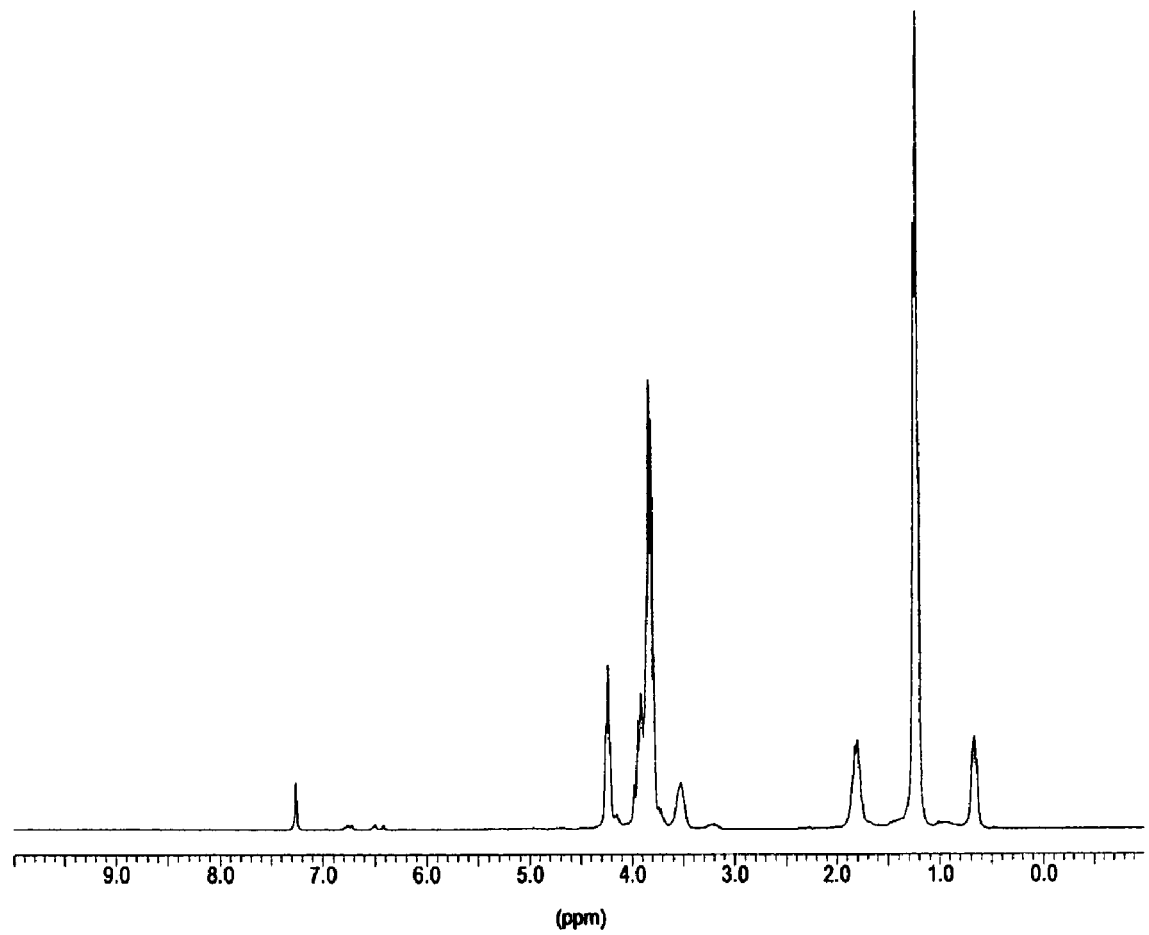
FIG. 1 is the $^1$H-NMR spectrum of the compound obtained in Practical Example 1.

The invention claimed is:

1. An organic silicon compound represented by the following general formula:

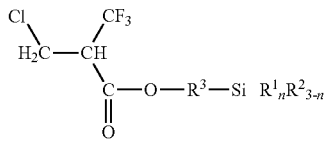

wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^3$ designates a substituted or unsubstituted alkylene group having 1 to 20 carbon atoms, and "n" is an integer from 0 to 3.

2. The organic silicon compound of claim 1, in which $R^3$ designates a substituted or unsubstituted alkylene group having 2 to 20 carbon atoms.

3. A method of manufacturing an organic silicon compound represented by the following general formula:

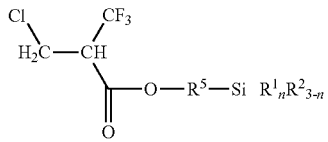

wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^5$ designates a substituted or unsubstituted alkylene group having 2 to 20 carbon atoms, and "n" is an integer from 0 to 3, the method being characterized by carrying out a reaction between a compound of the following general formula:

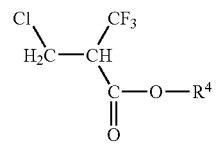

wherein, $R^4$ designates an alkenyl group with 2 to 20 carbon atoms and a silicon compound having a silicon-bonded hydrogen atom and represented by the following general formula:

$$R^1{}_n R^2{}_{3-n} SiH$$

wherein, $R^1$, $R^2$, and "n" are the same as defined above, with the reaction being carried out in the presence of a hydrosilylation catalyst.

4. A method of manufacturing an organic silicon compound that contains a (2-trifluoromethylacryloxy) alkyl group and is represented by the following general formula:

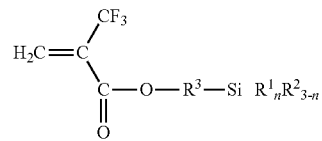

wherein, $R^1$ independently designates the same or different substituted or unsubstituted hydrocarbon groups having 1 to 20 carbon atoms, $R^2$ independently designates the same or different groups selected from halogen groups or hydrolysable groups having 1 to 20 carbon atoms, $R^3$ designates substituted or unsubstituted alkylene groups having 1 to 20 carbon atoms, and "n" is an integer from 0 to 3, the method being characterized by carrying out a reaction between a basic compound and an organic silicon compound of the following general formula:

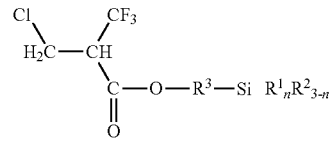

wherein, $R^1$, $R^2$, $R^3$, and "n" are the same as defined above.

* * * * *